US011684585B2

(12) United States Patent
Ortac et al.

(10) Patent No.: US 11,684,585 B2
(45) Date of Patent: *Jun. 27, 2023

(54) NANOSCALE COATINGS FOR ENCAPSULATION OF BIOLOGICAL ENTITIES

(71) Applicant: The Regents of the University of California, Oakland, CA (US)

(72) Inventors: Inanc Ortac, San Diego, CA (US); Gen Yong, Bedok (SG); Michael Benchimol, San Diego, CA (US); Sadik C. Esener, Solana Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/118,509

(22) Filed: Dec. 10, 2020

(65) Prior Publication Data
US 2021/0093580 A1    Apr. 1, 2021

Related U.S. Application Data

(60) Continuation of application No. 16/255,709, filed on Jan. 23, 2019, now Pat. No. 10,869,841, which is a division of application No. 14/785,611, filed as application No. PCT/US2014/034723 on Apr. 18, 2014, now abandoned.

(60) Provisional application No. 61/813,612, filed on Apr. 18, 2013.

(51) Int. Cl.
| | |
|---|---|
| *A61K 9/51* | (2006.01) |
| *A61K 35/76* | (2015.01) |
| *A61K 38/00* | (2006.01) |
| *A61K 35/74* | (2015.01) |

(52) U.S. Cl.
CPC .......... *A61K 9/5192* (2013.01); *A61K 9/5115* (2013.01); *A61K 9/5146* (2013.01); *A61K 35/76* (2013.01); *A61K 35/74* (2013.01); *A61K 38/00* (2013.01)

(58) Field of Classification Search
CPC .. A61K 9/5192; A61K 9/5115; A61K 9/5146; A61K 35/76; A61P 35/00
See application file for complete search history.

(56) References Cited

U.S. PATENT DOCUMENTS

| | | | | |
|---|---|---|---|---|
| 10,869,841 B2 * | 12/2020 | Ortac | ................. | A61K 9/5192 |
| 2007/0243259 A1 | 10/2007 | Sung et al. | | |
| 2011/0229576 A1 * | 9/2011 | Trogler | ................. | A61K 9/14 424/193.1 |
| 2013/0336891 A1 | 12/2013 | Dayton et al. | | |
| 2015/0359871 A1 | 12/2015 | Stedman et al. | | |
| 2016/0067191 A1 | 3/2016 | Ortac et al. | | |
| 2017/0252413 A1 | 9/2017 | Esener et al. | | |

FOREIGN PATENT DOCUMENTS

| | | |
|---|---|---|
| EP | 2118006 B9 | 1/2013 |
| JP | 2007514519 | 6/2007 |
| WO | 2001080823 | 11/2001 |
| WO | 2002080977 | 10/2002 |
| WO | 2003034979 | 5/2003 |
| WO | 2005057163 | 6/2005 |
| WO | 2011096408 | 8/2011 |
| WO | 2012094541 | 7/2012 |
| WO | 2012142625 | 10/2012 |
| WO | 2014121132 | 8/2014 |

OTHER PUBLICATIONS

Alemany, R. et al., "Replicative adenoviruses for cancer therapy", Nature biotechnology 18, (2000) pp. 723-727.
Avgoustakis, "Pegylated Poly(Lactide) and Poly(Lactide-Co-Glycolide) Nanoparticles: Preparatation, Properties and Possible Applications in Drug Delivery", Current Drug Delivery, 2004, ppp. 321-333.
Balkundi, et al., "Encapsulation of Bacterial Spores in Nanooraganized Polyelectrolyte Shells," Langmuir, vol. 25, No. 24, Dec. 15, 2009, pp. 14011-14016.
Beer et al, "Poly (lactic-glycolic) acid copolymer encapsulation of recombinant adenovirus Yeduces immunogenicity in vivo", Gene Therapy 5 (1998) pp. 740-746.
Chen, Y. et al., "Pre-existent adenovirus antibody inhibits systemic toxicity and antitumor activity of CN706 in the nude mouse LNCaP xenograft model: implications and proposals for human therapy", Human gene therapy 11, (2000) pp. 1553-1567.
EPO, European Rule 94 Communication for European Patent Application No. 14785811.2; dated Nov. 14, 2017, 7 pages.
EPO, European Rule 94 Communication for European Patent Application No. 14785811.2; dated Nov. 2, 2018, 8 pages.
EPO, Extended European Search Report for European Patent Application No. 20163230.4, dated Jul. 16, 2020. 12 pages.
EPO, Extended European Search Report for European Patent Application No. 14785811.2; dated Dec. 14, 2016; 9 pages.
Ferguson, M. S. et al., "Systemic delivery of oncolytic viruses: hopesand hurdles", Advances in virology 2012, 14 pages.
Fisher, K. D. et al. "Polymer-coated adenovirus permits efficient retargeting and evades neutralising antibodies". Gene Therapy 8, (2001), pp. 341-348.

(Continued)

*Primary Examiner* — Anna R Falkowitz
(74) *Attorney, Agent, or Firm* — Perkins Coie LLP

(57) ABSTRACT

Methods, systems, and devices are disclosed for encapsulating biological entities with preservation of their biological activity. In one aspect, a method of encapsulating a biological entity includes templating a biocompatible material onto a biological structure to form a coating structure enclosing the biological structure, the coating structure having a size in the nanometer range, in which the coated biological structure preserves its biological activity within the coating structure. In some implementations of the method, the biological structure includes a virus and the biocompatible material includes silica.

15 Claims, 8 Drawing Sheets

(56) References Cited

OTHER PUBLICATIONS

Guan, H. H. et al. "Liposomal formulations of synthetic MUC1 peptides: effects of encapsulation versus surface display of peptides on immune responses", Bioconjugate chemistry 9, (1998) pp. 451-458.

Heo, J. et al. "Randomized dose-finding clinical trial of oncolytic immunotherapeutic vaccinia JX-594 in liver cancer", Nature Medicine 1-10 (2013).doi:10.1038/nm.3089.

Ikeda, K. et al., "Oncolytic virus therapy of multiple tumors in the brain requires suppression of innate and elicited antiviral responses", Nature Medicine 5, (1999) pp. 881-887.

ISA, International Search Report and Written Opinion of International Application No. PCT/US2014/034723; dated Sep. 16, 2014; 12 pages.

Jokerst et al., "Nanoparticle PEGylation for imaging and therapy", Nanomedicine, 2011, 6(4), pp. 715-728.

JPO, Office Action for Japanese Patent Application No. 2016-509139, dated Jan. 30, 2018, 11 pages.

JPO, Office Action for Japanese Patent Application No. 2016-509139, dated Sep. 27, 2018, 3 pages.

Kaehr et al., "Cellular complecity captured in durable cilica biocomposites", PNAS, 2012, vol. 109, pp. 17336-17341.

Kangasniemi et al, "Extended release of adenovirus from silica implants in vitro and in vivo" Gene Therapy 16, (2009) pp. 103-110.

Kaufman, H. L. et al. "Local and distant immunity induced by intralesional vaccination with an oncolytic herpes virus encoding GM-CSF in patients with stage IIIc and IV melanoma", Annals of surgical oncology 17, (2010) pp. 718-730.

Kiessling, L. L. et al., "Synthetic multivalent ligands in the exploration of cell-surface interactions", Current opinion in chemical biology 4, (2000) pp. 696-703.

Kirn, D., "Clinical research results with dl1520 (Onyx-015), a replication-selective adenovirus for the treatment of cancer: what have we learned?" Gene Therapy 8, (2001) pp. 89-98.

Liberman et al. "Synthesis and surface functionalization of silica nanoparticles for nanomedicine" Surface Science Reports, 2014, vol. 69, pp. 132-158.

Liu, T.-C. et al., "Systemic efficacy with oncolytic virus therapeutics: clinical proof-of-concept and future directions", Cancer Research 67, (2007) pp. 429-432.

Matthews, R.E.F. "A Classification of Virus Groups Based on the Size of the Particle in Relation to Genome Size" J. Gen. Virol. 1975, vol. 27, pp. 135-149.

Morrison, J. et al., "Virotherapy of ovarian cancerwith polymer-cloaked adenovirus retargeted to the epidermal growth factor receptor". Moleculartherapy the journal ofthe American Society of Gene Therapy 16, (2008) pp. 244-251.

Mykhaylyk et al., "Silica-Iron Oxide Magnetic Nanoparticles Modified for Gene Delivery: A Seach for Optimum and Quantitative Criteria", Pharm. Res., 2002, pp. 1344-1365.

Pandha, H. et al., "Oncolytic viruses: time to compare, contrast, and combine?" American Society of Gene Therapy 17, (2009), pp. 934-935.

Parato, K. et al., "Recent progress in the battle between oncolytic viruses and tumours", Nature Reviews Cancer 5, (2005) pp. 965-976.

Royston et al, "Characterization of silica-coated tobacco mosaic virus", Journal of Colloid and Interface Science 298 (2006) pp. 706-712.

Sailaja et al, "Encapsulation of recombinant adenovirus into alginate microspheres circumvents vector-specific immune response", Gene Therapy 9 (2002) pp. 1722-1729.

Science Direct, "Virus Particle—an overview" retrieved from https://www.sciencedirect.com/topics/medicine-and-dentistry/virus-particle April 10, 2020. 13 pages.

Shenton et al., "Inorganic±Organic Nanotube Composites from Template mineralization of Tobacco Mosaic Virus", Adv. Mater. 1999, 11, No. 3, pp. 253-256.

Slowing et al. "Mesoporous Silica Nanoparticles for Drug Delivery and Biosensing Applications" Advanced Functional Materials, 2007, vol. 17, pp. 1225-1236.

Tang, F. et al., "Mesoporous silica nanoparticles: synthesis, biocompatibility and drug delivery", Advanced materials (Deerfield Beach, Fla.) 24, (2012) pp. 1504-1534.

Toyoda et al, "Cationic Polymer and Lipids Enhance Adenovirus-Mediated Gene Transfer to Rabbit Carotid Artery", Stroke 29 (1998) pp. 2181-2188.

Tsai, V. et al., "Impact of human neutralizing antibodies on antitumor efficacy of an oncolytic adenovirus in a murine model", Clinical Cancer Research 10, (2004) pp. 7199-7206.

Wang et al, "Chitosan Modification of Adenovirus to Modify Transfection Efficiency in Bovine Corneal Epithelial Cells", PLoS ONE5 (2010) e12085.

Wang, C.-H. K. et al., "The transduction of Coxsackie and Adenovirus Receptor-negative cells and protection against neutralizing antibodies by HPMA-co-oligolysine copolymer-coated adenovirus", Biomaterials 32, (2011) pp. 9536-9545.

Wein, L. M. et al., "Validation and analysis of a mathematical model of a replication-competent oncolytic virus for cancer treatment: implications for virus design and delivery", Cancer Research 63, (2003) pp. 1317-1324.

Yang, Y. et al., "Transient subversion of CD40 ligand function diminishes immune responses to adenovirus vectors in mouse liver and lung tissues", Journal of Virology, 1996, pp. 6370-6377.

Yong, et al. "Biocompatible Coating to Enable Immune Evasion for Viral Therapy," poster, University of California, San Diego Medical Center, Department of NanoEngineering (2013), 1 page.

EPO, Examination Report for European Application No. 20163230.4, dated Jun. 7, 2022. 6 pages.

* cited by examiner

NANOSCALE COATINGS FOR ENCAPSULATION OF BIOLOGICAL ENTITIES

CROSS-REFERENCE TO RELATED APPLICATIONS

This patent document is a continuation of U.S. patent application Ser. No. 16/255,709, titled "NANOSCALE COATINGS FOR ENCAPSULATION OF BIOLOGICAL ENTITIES" and filed on Jan. 23, 2019, which is a divisional of U.S. patent application Ser. No. 14/785,611, entitled "NANOSCALE COATINGS FOR ENCAPSULATION OF BIOLOGICAL ENTITIES" and filed on Oct. 19, 2015, which is a 35 U.S.C. § 371 National Stage application of International Application No. PCT/US2014/034723, entitled "NANOSCALE COATINGS FOR ENCAPSULATION OF BIOLOGICAL ENTITIES" and filed on Apr. 18, 2014, which further claims benefit of priority of U.S. Provisional Patent Application No. 61/813,612, entitled "NANOSCALE COATINGS FOR ENCAPSULATION OF BIOLOGICAL ENTITIES" and filed on Apr. 18, 2013. The entire contents of the aforementioned patent applications are incorporated by reference as part of the disclosure of this patent document.

TECHNICAL FIELD

This patent document relates to nanoscale materials and nanotechnologies.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem can exhibit various unique properties, e.g., including optical properties, that are not present in the same materials at larger dimensions and such unique properties can be exploited for a wide range of applications.

SUMMARY

Techniques, systems, devices, and materials are described for encapsulating biological entities with preservation of their biological activity.

In one aspect, a method to produce a bioactive payload delivery device includes forming an intermediate structure by binding a polymer material with a biological substance based on an electrostatic force, in which the formed intermediate structure includes a plurality of regions presenting a net surface charge, and forming a coating structure of a biocompatible material directly on the formed intermediate structure to enclose the biological substance, in which the coating structure preserves biological activity of the biological substance enclosed therein, thereby producing a bioactive payload delivery device.

In another aspect, a bioactive payload delivery device includes an interior material structure including a polymer material and a biological substance that are bound to each other via an electrostatic interaction, in which the interior material structure includes a plurality of regions presenting a net surface charge, and an exterior nanostructure formed of a biocompatible material to encapsulate the interior structured material, thus preserving biological activity of the encapsulated biological substance.

In another aspect, a method for encapsulating a biological substance includes forming a biocompatible material onto a biological structure to form a coating structure enclosing the biological structure, the coating structure having a size in the nanometer range, in which the biological structure preserves biological activity within the coating structure. In some implementations of the method, the biological structure includes a virus and the biocompatible material includes silica.

The subject matter described in this patent document can be implemented in specific ways that provide one or more of the following features. The disclosed methods can be implemented to encapsulate biological entities or other substances within a synthetic matrix, e.g., such as silica in a nanoparticle format, where the encapsulated bioentities are without any loss or with minimal loss of their activity. The synthesized nanostructured matrix (e.g., silica nanoparticle enclosure) provides the ability to target the release of the biologicals, e.g., through an externally triggered mechanism and/or incorporation of targeting moieties to the synthesized nanostructured matrix. In some implementations, the method can include effectively changing the surface charge on the biological entity through cross reaction with a cationic polymer like poly-L-lysine. The method can include a charge mediated silica sol-gel condensation reaction directly onto the surface of the biological entities, e.g., forming an enveloping silica matrix coating around the biologicals giving rise to a nanoparticle. In some implementations, for example, a sensitizing agent such as fluorocarbon emulsions can be used as ultrasound triggered cavitation centers and be co-encapsulated with the biological entities, e.g., bound to the biological entity prior to the exemplary silica sol-gel condensation reaction to allow for an externally triggered release mechanism to be built into the nanoparticle. For example, once the nanoparticle is formed, additional surface modifications can be made to the nanoparticle using various chemistries including silane chemistry to add a variety of functional characteristics to the nanoparticle, including, but not limited to, polyethylene glycol (PEG) for immune response evasion, targeting moieties for specific delivery or release, environmental sensing moieties (e.g., redox, hypoxic, acidic, etc.) for targeted release. Since the exemplary synthetic nanostructured matrix prevents the encapsulated biological entities from being directly exposed to serum and tissue conditions prior to being released, the encapsulated biological entities are protected from degrading conditions present in serum, e.g., allowing for an enhanced activity half-life in vivo. Also, for example, the ability to selectively trigger the release of the biologicals results in lower systemic toxicity giving rise to a better tolerated therapy regime.

For example, the disclosed biocompatible coating nanostructure can be easily functionalized and utilized to encapsulate biological entities such as viruses (e.g., adenoviruses). Exemplary implementations using scanning electron microscopy (SEM) analysis to characterize exemplary coating nanostructures shows discrete mono-disperse particles with nanoscale features. Exemplary implementations also showed that exemplary nanostructure-coated viruses retained transduction ability and were protected from proteinase k and neutralizing antibodies. Additionally, for example, implementations of the disclosed technology showed the ability to ablate uptake of the exemplary coated virus by functionalizing the exemplary coating with polyethylene glycol (PEG). For example, subsequent conjugation of cRGD to the exemplary coating rescued the transduction ability of the viruses. The exemplary coating is robust, and the coated virus can be stored at −80° C. without loss in activity. Applications of the disclosed technology can include, but are not limited to, biotechnology and biomedicine, e.g., such as in the treatment and monitoring of numerous diseases including cancer, diabetes, among others. For example, the disclosed technology can be used as a therapeutic approach for clinical translation with the goal of opening up the use of oncolytic viruses to more cancer therapeutic applications and improving the clinical response rates of oncolytic viruses. Furthermore, the disclosed nanocoating platform may enable additional gene therapy based approaches targeted at cancer metabolism and other genetic based diseases.

Those and other features are described in greater detail in the drawings, the description and the claims.

DETAILED DESCRIPTION

Figure 1A:
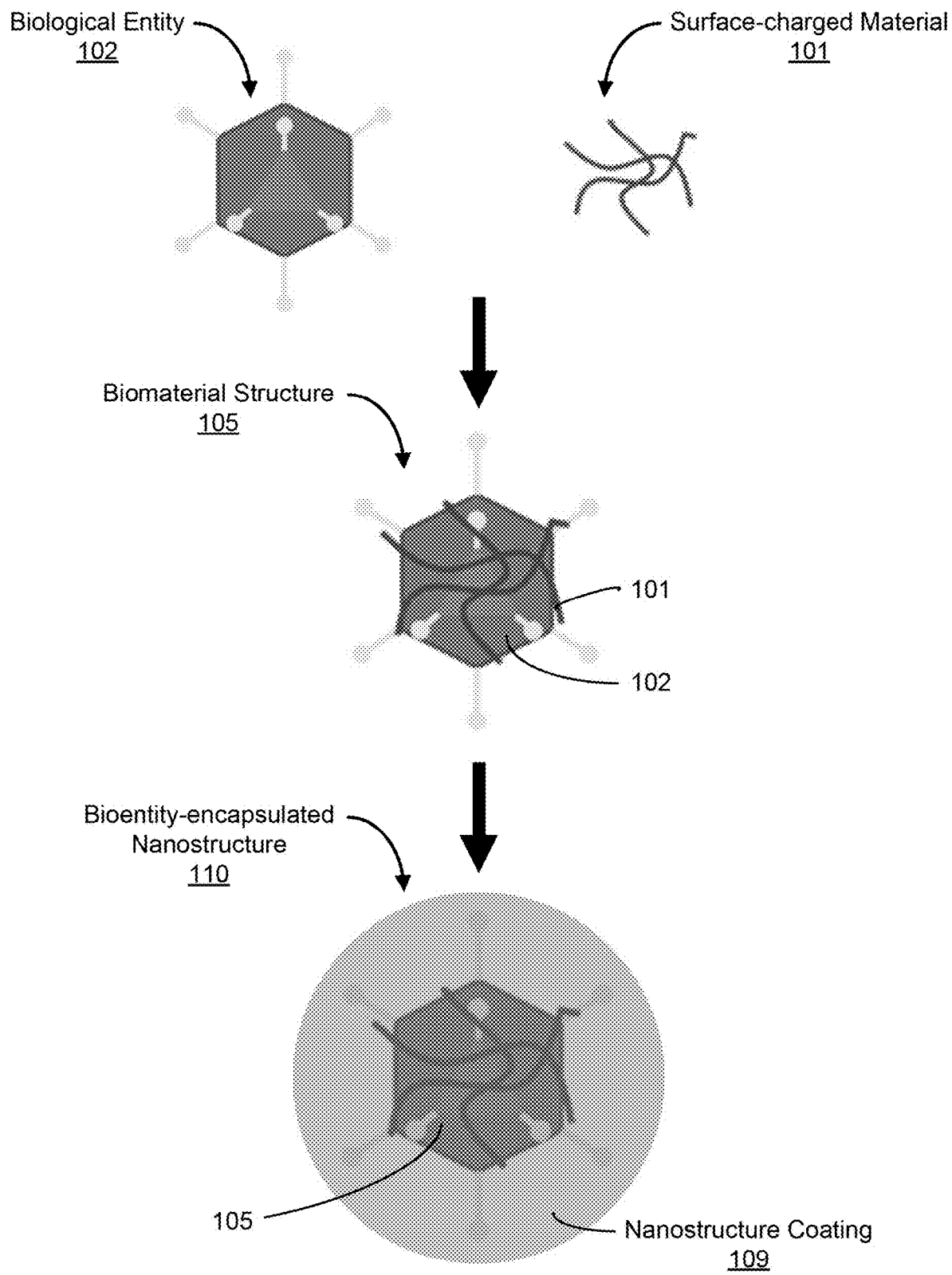
FIG. 1A shows an illustrative diagram of the exemplary method for a nanoscale template driven encapsulation process of biological entities that preserves biological activity.

Oncolytic viral therapy is a cancer therapy that uses viruses to selectively replicate in and kill tumor cells. Over the last two decades, significant progress has been made in the preclinical and clinical development of viral-based therapy as a platform for the treatment of cancer. While much progress has since been made in understanding viral lifecycles and biology, their delivery and clearance characteristics remain a major stumbling block for effective therapy. For example, some patients mount immune response to the viral therapy, e.g., which can cause and increase side effects in treatment of the patient, and overall, limits the clinical efficacy of this therapeutic approach. Current methods to address the challenges of viral therapy techniques such as immune response focuses on direct modification of virus, or encapsulation. Also, harsh chemical reaction conditions during treatment also impact viability of the viral therapy. For example, efficacy of viral therapy also depends on natural affinity of viral vectors for target cells (e.g., host cell tropism). It is believed that the ability to effectively deliver therapeutic viruses systemically need technology to address these challenges and thereby expand the efficacy of the oncolytic viral platform to patients with disseminated disease.

Techniques, systems, devices, and materials are described for encapsulating biological entities using nanoscale material designs and specialized functionalization. Implementations of the disclosed technology include biocompatible nanocoatings that preserve the bioactivity of a viral payload and protect the viral payload from immune recognition and neutralization during viral therapy treatment, with specific targeting, improved circulation, and theranostic abilities.

In some aspects, the disclosed technology includes a nanoscale template fabrication process to encapsulate a biological entity (e.g., such as a virus) in an nanostructured enclosure (e.g., such as a nanoparticle coating structure). In addition to encapsulating the biological entity, the nanostructured enclosure also has the ability to target the release of the biological entity through an external trigger and/or the incorporation of targeting moieties in the nanostructure enclosure. For example, the disclosed technology can be applied in a variety of fields in biomedicine and biotechnology, e.g., including viral therapies.

In some implementations, a viral vector can be encapsulated in a silica-based nanoparticle coating structured to provide a controlled release mechanism to target the release of the virus payload, in vitro and in vivo, using an external trigger and/or incorporated target moieties. In some examples, an external acoustic signal can be applied to the exemplary nanostructured coating containing the viral vector to cause release of the viral vector at a target site within an organism, e.g., such as at a tumor within an animal.

Exemplary implementations using adenoviruses encapsulated by the exemplary silica nanocoating structures are described, e.g., conferring protection against proteinase K. For example, results of the exemplary implementations as shown herein demonstrated activation using ultrasound of viral transfection in a human pancreatic cell line. In other implementations, for example, the disclosed encapsulation approach can be adopted for materials other than silica, e.g., including, but not limited to, titanium oxide and calcium phosphate.

In some implementations, for example, the exemplary silica-based nanoparticle coating can be formed by the direct condensation of a removable silica matrix on the surface of biological entities to form the nanoparticle while preserving biological activity. Using the disclosed fabrication techniques, for example, the exemplary silica matrix can be formed directly on the surface of the biological entities under biologically compatible reaction conditions. This allows higher encapsulation efficiency without consequent loss of activity of the biological entities. This also brings fine control over particle size giving nanoparticles with well-defined size characteristics. For example, silica can be used to form the nanostructure coating, e.g., particularly in biological applications due to its biocompatibility and biodegradability. Additionally, for example, the disclosed technology can include a sensitizing agent within the synthesized structure to allow externally triggered release of the encapsulated biological entities, as well as exemplary methods for the functionalization of the nanoparticle for exemplary characteristics like improved circulation time and targeting benefiting from easy functionalization of silica surface.

In some aspects, the disclosed technology includes a method of encapsulating biological entities and biological substances within a synthetic matrix, e.g., such as silica in a nanoparticle format, without any loss or with minimal loss of activity of the biological entities or substances. For example, the produced synthetic matrix enclosure (e.g., nanoparticle) encapsulating the biological entities or substances can be configured to have the ability to selectively release the biological entities or substances through an externally triggered mechanism and/or the incorporation of targeting moieties to the synthetic matrix enclosure. For example, the exemplary method can include a process for templating silica onto biological entities, e.g., viruses, while preserving biological activity/compatible with life. In some implementations, the method can include a process for changing the surface charge on the biological entities, e.g., through cross reaction with a poly-cationic substrate (e.g., such as poly-l-lysine) to a positively charged surface compatible with the silica polycondensation process. In some implementations, the method can include a process to implement a charge mediated silica sol-gel condensation reaction directly onto the surface of the biological entities or substances forming an enveloping silica matrix coating around the biological entities or substances giving rise to a nanoparticle. For example, a sensitizing agent such as fluorocarbon emulsions as ultrasound triggered cavitation centers can be included prior to the silica sol-gel condensation reaction to allow for an externally triggered release mechanism to be built into the particle. In some implementations, the method can include a process to encapsulate a drug or a therapeutic agent with the biological entity. In some implementations, the method can include a process to include iron oxide or other materials (of a nano-particulate nature) into the produced silica coating, e.g., for imaging. Once the nanoparticle is formed, for example, the method can include implementing additional surface modifications to the nanoparticle using various chemistries, e.g., including silane chemistry to add a variety of functional characteristics to the nanoparticle, e.g., such as PEG for immune evasion, targeting moieties for specific delivery or release, environmental sensing moieties (e.g., redox, hypoxic, acidic, etc.) for targeted release, among others. For example, since the biologicals are not being directly exposed to serum and tissue conditions prior to being released, the encapsulated biologicals are protected from degrading conditions present in serum allowing for an enhanced activity half-life in vivo. For example, the ability to selectively trigger the release of the biologicals results in lower systemic toxicity giving rise to a better tolerated therapy regime. In some implementations, the method can include stabilizing the encapsulated biological entity allowing for improved thermal stability at $-80°$ C. to $-37°$ C. For example, lyophilization or critical point drying of the nanoparticle can be performed while preserving the biological activity of the encapsulated entity.

Figure 1B:
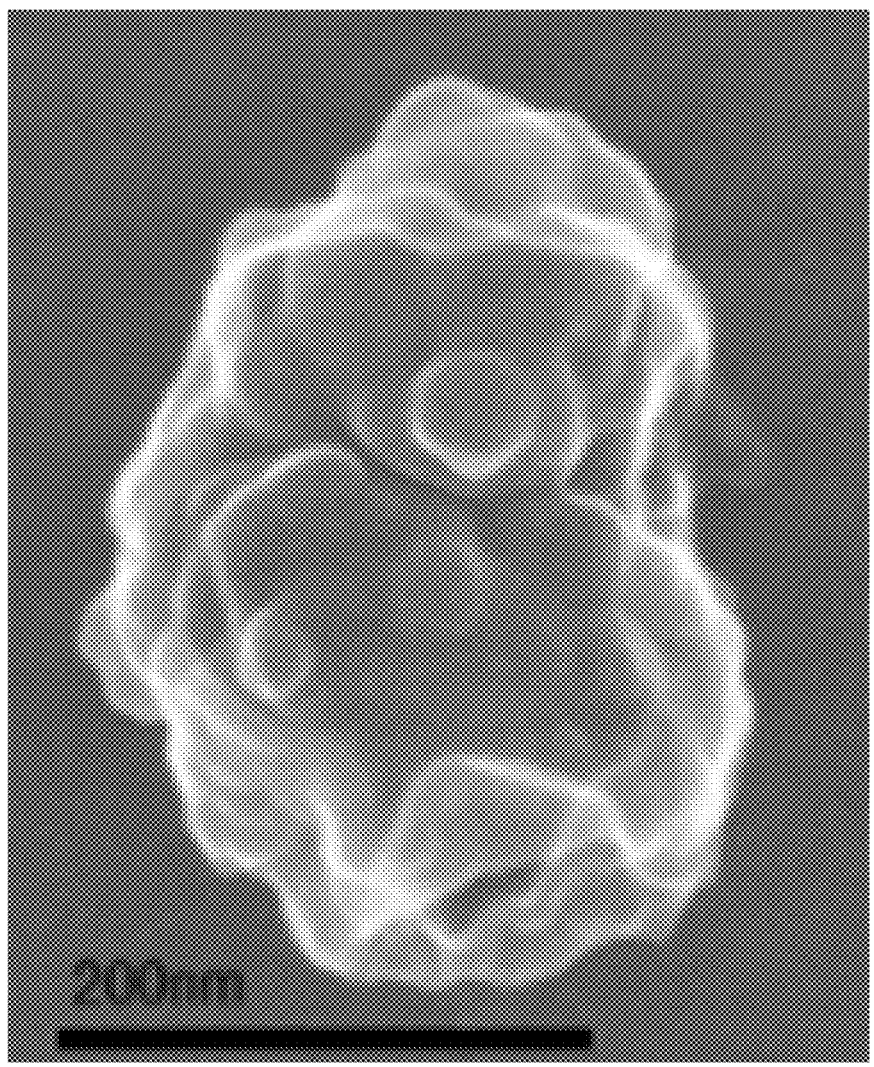
FIG. 1B shows a scanning electron microscopy (SEM) image of an exemplary silica nanostructure coating of a virus.

FIG. 1A shows an illustrative diagram of the exemplary method for a nanoscale template driven encapsulation process of biological entities that preserves the biological activity of the encapsulated biological entities. The method includes a process to form an intermediary biomaterial structure 105 by binding a surface-charged material 101 with a biological entity or substance 102 such that the formed intermediary biomaterial structure 105 presents regions having a net surface charge, e.g., which may be modified from that of the biological entity substance 102. For example, as illustrated in the diagram of FIG. 1A, a negatively charged virus (e.g., adenovirus) is reacted with a cationic polymer, poly-L-lysine (PLL), to modify the surface charge on the adenovirus, e.g., in which the PLL is bound to the surface of the adenovirus by an electrostatic force. The method includes a process to form biological entity-encapsulated nanostructure 110 by forming a nanostructure coating 109 to enclose the intermediary biomaterial structure 105, in which the encapsulated bioentity or substance 102 maintains its bioactivity functionality. For example, as shown in FIG. 1A, the exemplary positively charged viral-material structure attracts negatively charged silica precursor and hydroxyl ions creating a basic environment suitable for a silica polycondensation reaction to form the nanostructure coating (e.g., silica-based nanoparticle) that encapsulates the viral payload. FIG. 1B shows an SEM image of an exemplary silica nanocoating of such viruses (e.g., referred to as a siVirus platform).

For example, silane chemistry is typically compatible with physiological conditions. The disclosed methods can manipulate silane chemistry to achieve coating of viruses into silica nanoparticles without any consequent loss of biological activity of the viruses, as shown later in FIGS. 2A-2C. Traditional sol gel synthesis methods use alkaline pH, acid catalysis or addition of salts. The subsequent gelation occurs in bulk in the liquid phase with downstream processing and aging of the gel to form silica compositions. Using the described fabrication methods, the sol gel reaction occurs at neutral pH and becomes template driven with the nanomaterial matrix (e.g., exemplary silica matrix) being formed directly on the surface of the biological entity to be encapsulated under biologically compatible reaction conditions.

In some implementations, for example, a charged template is used as an initial starting point of the reaction. Depending on the initial surface charge of the template, the template is re-functionalized to carry a net or partial positive charge via electrostatic interaction with a poly-cationic polymer like poly-L-lysine, e.g., thereby forming a biotemplate-material structure. Silicic acid is then added to the reaction mixture in a concentration where nucleation of bulk gelation of silica from sol occurs slowly. Absorption of silicic acid to the surface of the template occurs. When local concentration of silicic acid ions at the surface of the template surpasses the threshold for nucleation of silica gel, a self-limiting poly-condensation occurs on the surface of the template encasing the template in a matrix of silica gel. For example, the initial template can be accompanied by additional functional moieties for co-encapsulation. The reaction occurs at physiological conditions and allows higher encapsulation efficiency without consequent loss of activity of the biologicals. This also brings fine control over particle size giving nanoparticles with well-defined size characteristics. Additionally, for example, the silica coating can easily accept secondary functionalizations to achieve a broad range of material properties.

The exemplary method can include a wet-chemical fabrication process using silica sol-gel chemistry that uses a colloidal solution (sol) as a precursor for an integrated network (gel) of discrete particles or network of amorphous silica, e.g., such as:

$$Si(OCH_3)_4 + 2H_2O \rightarrow SiO_2 + 4CH_3OH.$$

Examples of possible functional moieties for added functions include, but are not limited to, nano-emulsions for ultrasound activation, chemotherapy drugs like doxorubicin, standard therapeutic drugs like statins, therapeutic compounds like small molecule inhibitors, DNA vectors, RNA vectors for shRNA and RNAi, microRNA, and MRI contrast agents like gadolinium and radio-contrast dyes.

Examples of secondary functionalization include, but are not limited to, PEG, pH sensitive PEG, affibodies, antibodies, IgG, IgM, targeting ligands like VEGF-C, cRGD and folate, DNA and aptamers, proteins, lipoproteins, apolipoproteins, glycoproteins, glycans, carbohydrates, saccharides and oligosaccharides, polymers and oligomers, and lipids.

The disclosed template-driven nanoencapsulation technology preserves biological activity of proteins, enzymes, DNA vectors, viruses, bacteria and other sensitive biological agents that would otherwise not be able to maintain biological activity in vivo to provide a degree of protection to the encapsulated agent. In some implementations, the present technology includes a template-driven silica polycondensation process to produce well defined particles with controllable size characteristics in the nanoscale regime. For example, the template-driven silica polycondensation process includes directly templating silica on the agent to be encapsulated, which can enable encapsulation of a broad range of agents without size constraints with very high efficiencies. The disclosed nanomaterial structures can be produced and utilized as (1) a biocompatible coating that allows for immune system evasion and protection from degradation; and (2) a scaffold to incorporate additional functional moieties, e.g., to retarget the virus, decrease biochemical affinity to inhibit adhesion and uptake (e.g., PEGylation, charge, zwitterionic), increase biochemical affinity with targeting ligands (e.g., mAb), or enabling ultrasound-triggering (e.g., perfluorocarbon nanoparticle, cavitation nucleation site).

In some exemplary implementations of the disclosed technology, viruses were encapsulated in silica nanocoating structures.

Viruses are highly evolved systems with gene transfer and lytic mechanisms that can be used for medicinal applications. However, there can be some technical issues to be addressed in such applications. For example, the immune system may be a barrier to these approaches, through its ability to recognize these viruses, neutralize them, and/or accelerate their clearance and degradation. Also, for example, the specific host cell tropism of viruses limits their application to specific cell populations. In this context of a viruses and other pathogens affecting a host tropism or cell tropism, tropism refers to the way in which different viruses/pathogens have evolved to preferentially target specific host species or cell types within a species.

Using oncolytic viruses as an example, oncolytic viruses can selectively replicate in and kill tumor cells, and over the last two decades significant progress has been made in the preclinical and clinical development of viral based therapy as a platform for the treatment of cancer. For example, the use of Onyx-015 demonstrated the safety of this approach, and significant responses were noted among patients treated by intralesional injections and regional vascular delivery. However, induction of high titers of neutralizing antibodies as well as high levels of antiviral cytokines was demonstrated among the cancer patients treated with Onyx-015, limiting the efficacy of this approach by systemic delivery. Despite these limitations, intratumoral and regional approaches are being pursued in large, multinational studies with growing evidence of success in melanoma and hepatocellular carcinoma. While much progress has been made in understanding viral lifecycles and biology, their delivery and clearance characteristics remain a major stumbling block for effective therapy. The human body is exceedingly effective in clearing most pathogens from circulation. While it may tolerate an initial dose of viruses for therapy, follow up doses are rapidly cleared with little therapeutic benefit. Additionally the issue of host cell tropism limits the utility of viruses only to cells with which they have affinities with. Addressing the issues of immune activation and host cell tropism would be key to advancing viral therapy. Implementations of the disclosed technology provides the ability to effectively deliver therapeutic viruses systemically and expand the efficacy of an oncolytic viral platform to patients with disseminated disease.

The issue of immune activation following viral therapy has been challenging to overcome. For example, it has been shown in animal models that prior exposure to a given virus limits therapeutic outcome in mice. Clinical trials of viral therapy in humans have noted the induction of high titers of neutralizing antibodies and elevated cytokine levels, which would limit the possibilities for their use in vivo. For example, viruses currently in clinical trials are derivative of common human pathogens that humans are exposed to on a regular basis. Prior exposure to these viruses complicates interpretation of the clinical outcome and negates the possibility of repeat therapy to clear residual disease. A secondary concern arising from immune activation is the short persistence time in blood and bioavailability of therapeutic viruses. The speed at which viruses are cleared from the immune system precludes general systemic delivery of therapeutic viruses. Most conventional approaches (e.g., in clinical trials) are focused on intratumoral, intralesional or intra-arterial delivery of viruses for regional therapy. The inability to achieve systemic delivery precludes the ability to properly treat disseminated and systemic diseases. The limitations on repeat dosing and lack of a true systemic therapy option from immune activation is a first and paramount hurdle that needs to be crossed for greater clinical uptake of viral therapy.

The issue of host cell tropism is particularly problematic because it implicates three areas of therapy, for example, the therapeutic targets that can be treated, variable receptor expression between patients, and off target toxicities. Just as flu virus that normally infects lung tissues would have difficulty gaining traction in the prostate or pancreas, individuals within a given population have different susceptibilities to different viral systems. Receptors that viruses use to gain entry into a cell have highly variable expression levels in cancer cells, which can lead to off target toxicities in tissues with high expression levels of these receptors (splenic and liver toxicities are often implicated).

The disclosed technology addresses the issue of immune activation and is able to retarget viruses to cell markers that are over expressed in disease conditions and expand the efficacy of the viral platform. Moreover, the disclosed technology opens up the use of viruses to more therapeutic applications to improve the clinical response rates. Furthermore, the disclosed siVirus platform enables additional gene therapy based approaches targeted at cancer metabolism and other genetic based diseases.

Changing the interaction surface a virus presents to the body impacts the type of response it elicits from downstream processes such as immune system responses and cellular uptake. In some embodiments of the disclosed nanocoating technology, silica is used, as it lends itself well as a coating material for viruses due to its favorable biocompatibility, degradation characteristics and flexible silane chemistry which allows for simple modification of the silica coating. Exemplary implementations using the exemplary silica nanocoating structures indicate that coating adenoviruses with silica improved their transduction ability with the silica layer rapidly degrading under endosomal conditions. Silica-coated viruses are also protected from neutralizing antibodies and proteinase K.

The disclosed technology can be used to change the interaction surface a virus presents to the body impacts the type of response it elicits from downstream processes like immune system responses and cellular uptake. In exemplary implementations performed and described herein, the ability to incorporate PEG and peptide components to ablate cellular uptake and achieve receptor mediated uptake respectively is demonstrated. For example, the exemplary silica coating is robust and the coated virus can be stored at −80° C. without loss in activity.

Figure 2A:
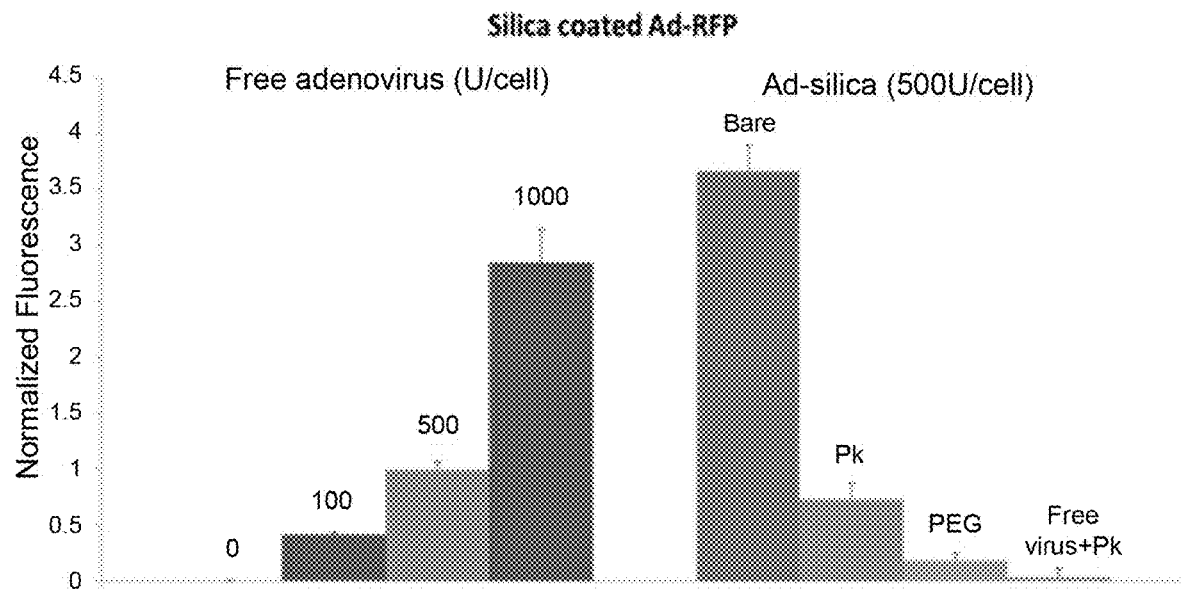
FIG. 2A-2C show data plots and images from exemplary implementations using the exemplary silica nanostructure coating encapsulating viruses.
Figure 2B:
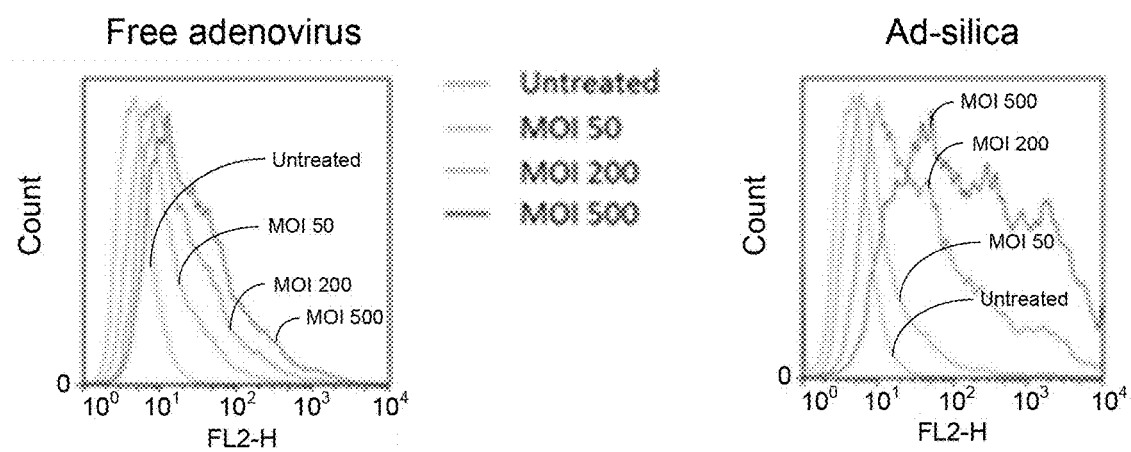
Figure 2C:
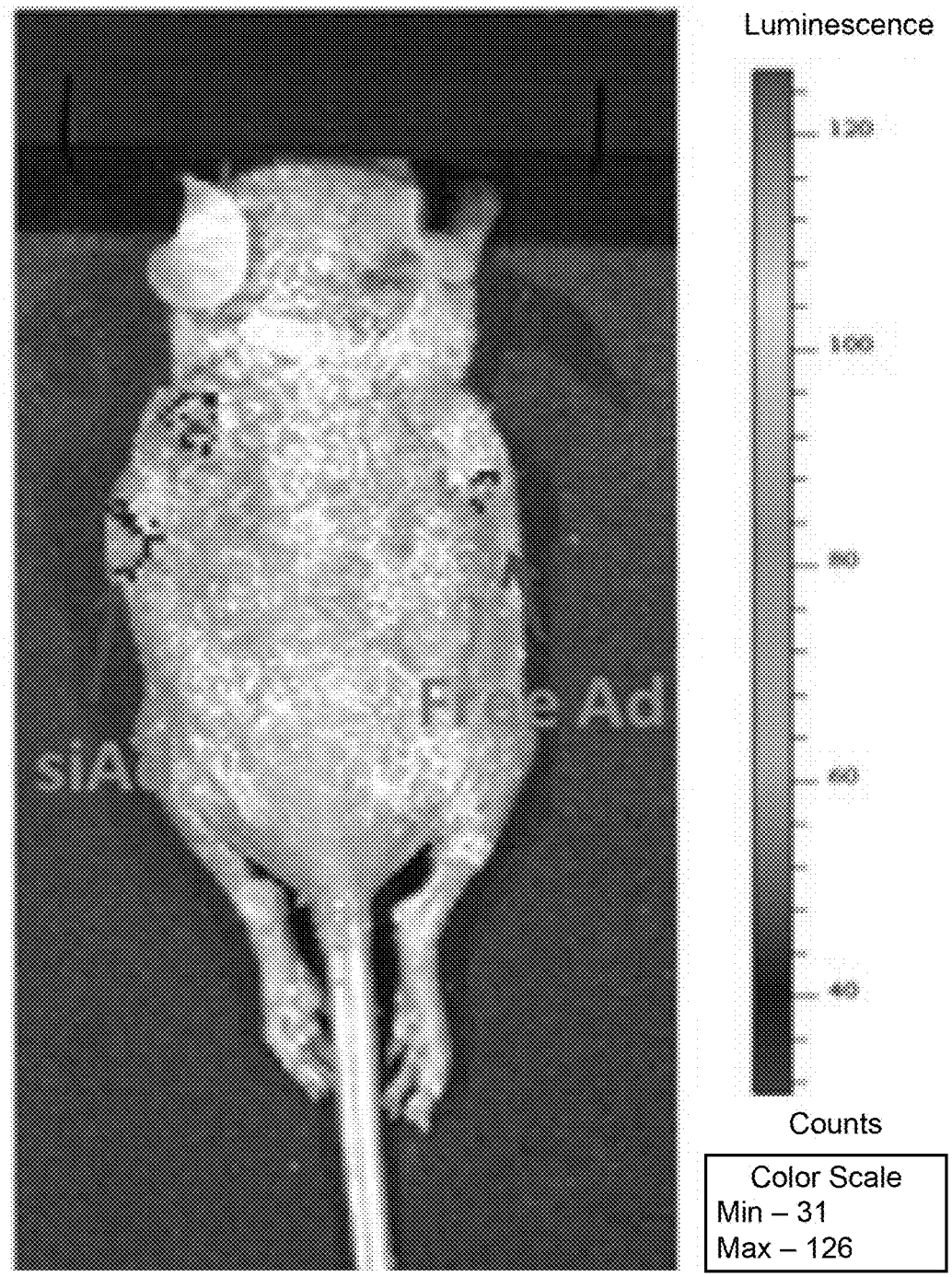
Figure 3:
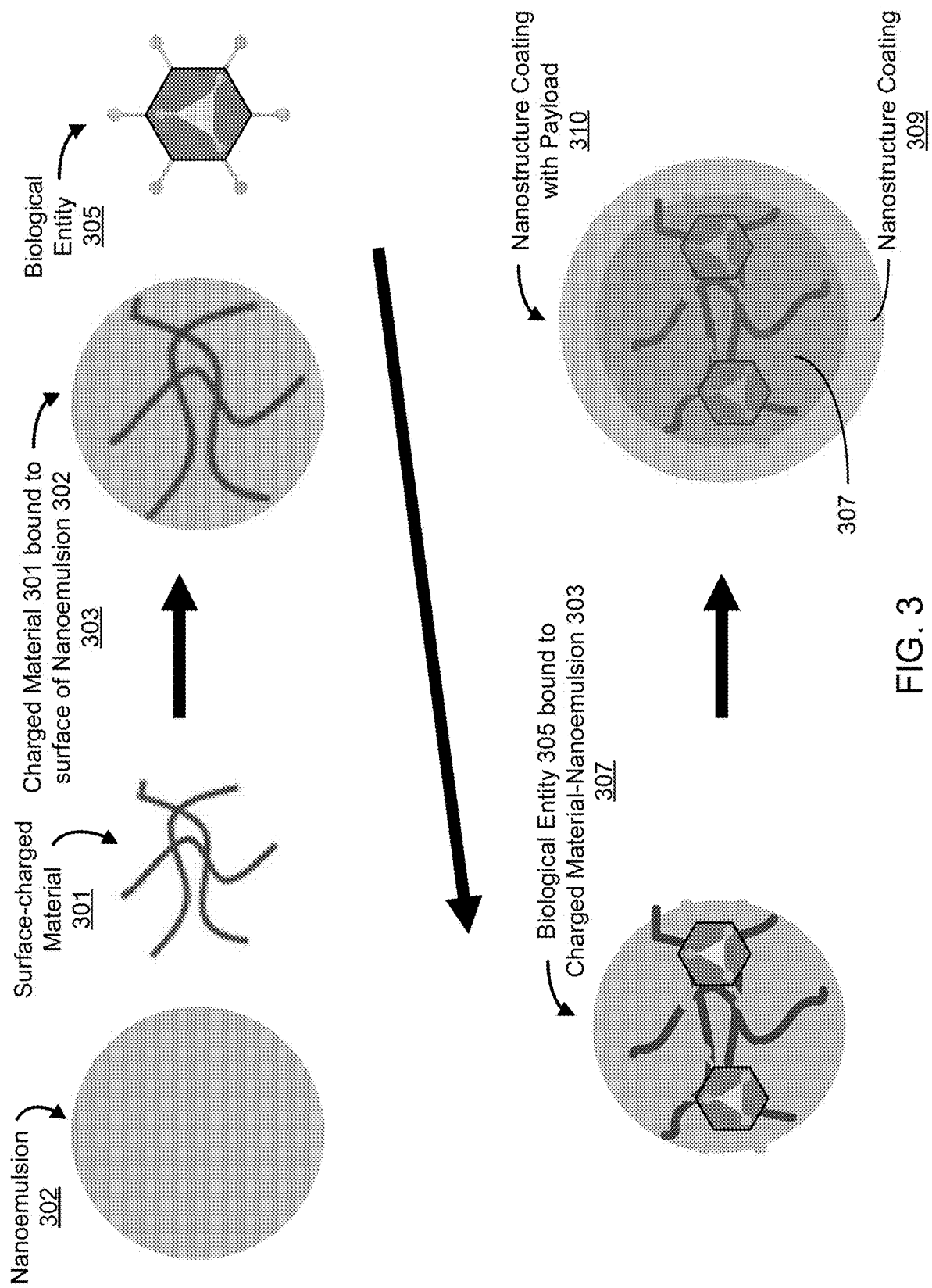
FIG. 3 shows a process diagram of an exemplary method for co-encapsulation of biological entities with targeting moieties in the nanostructure enclosure.
Figure 4:
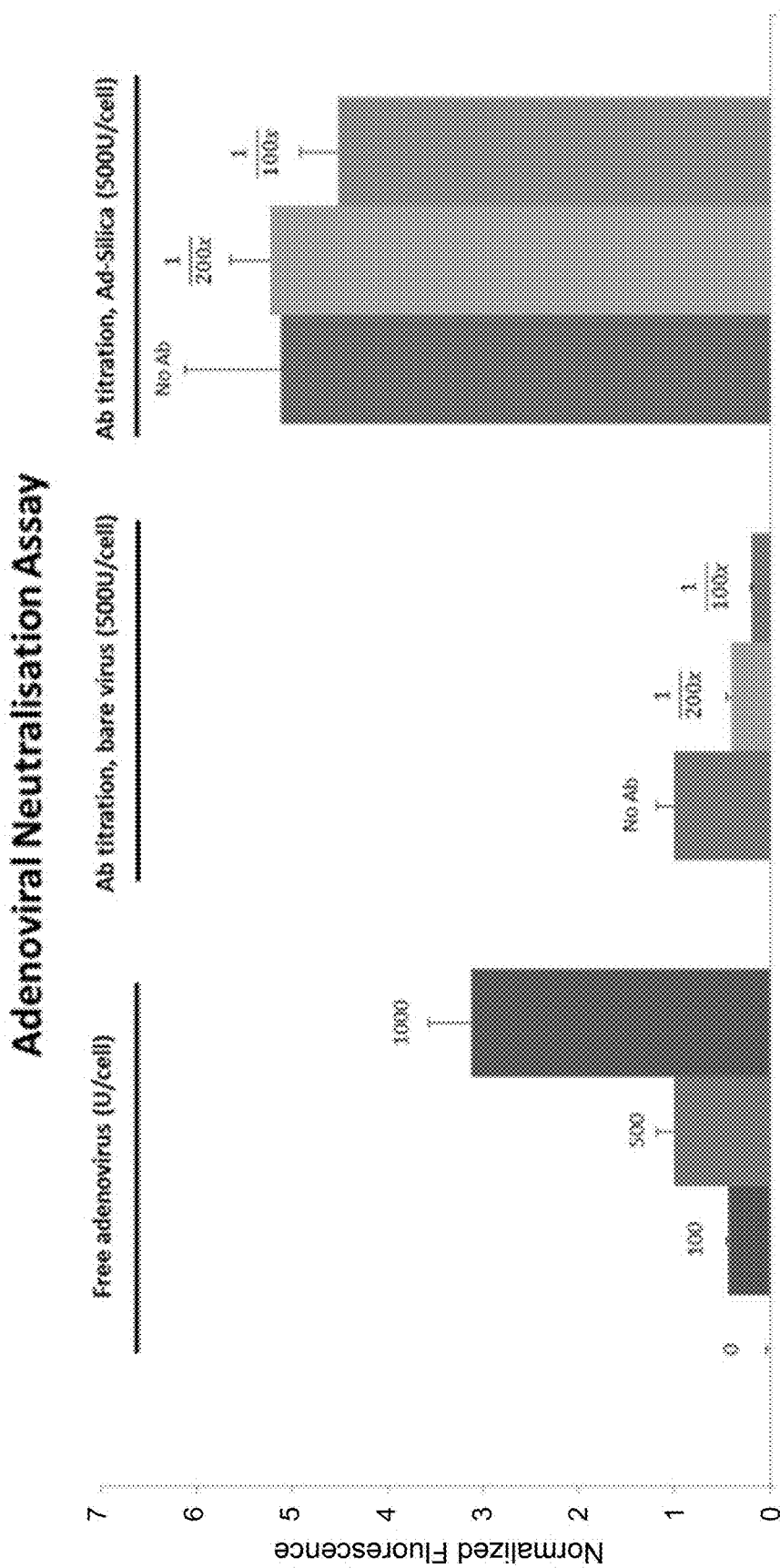
FIG. 4 shows data plots of an exemplary neutralization assay in the presence of antibodies.
Figure 5:
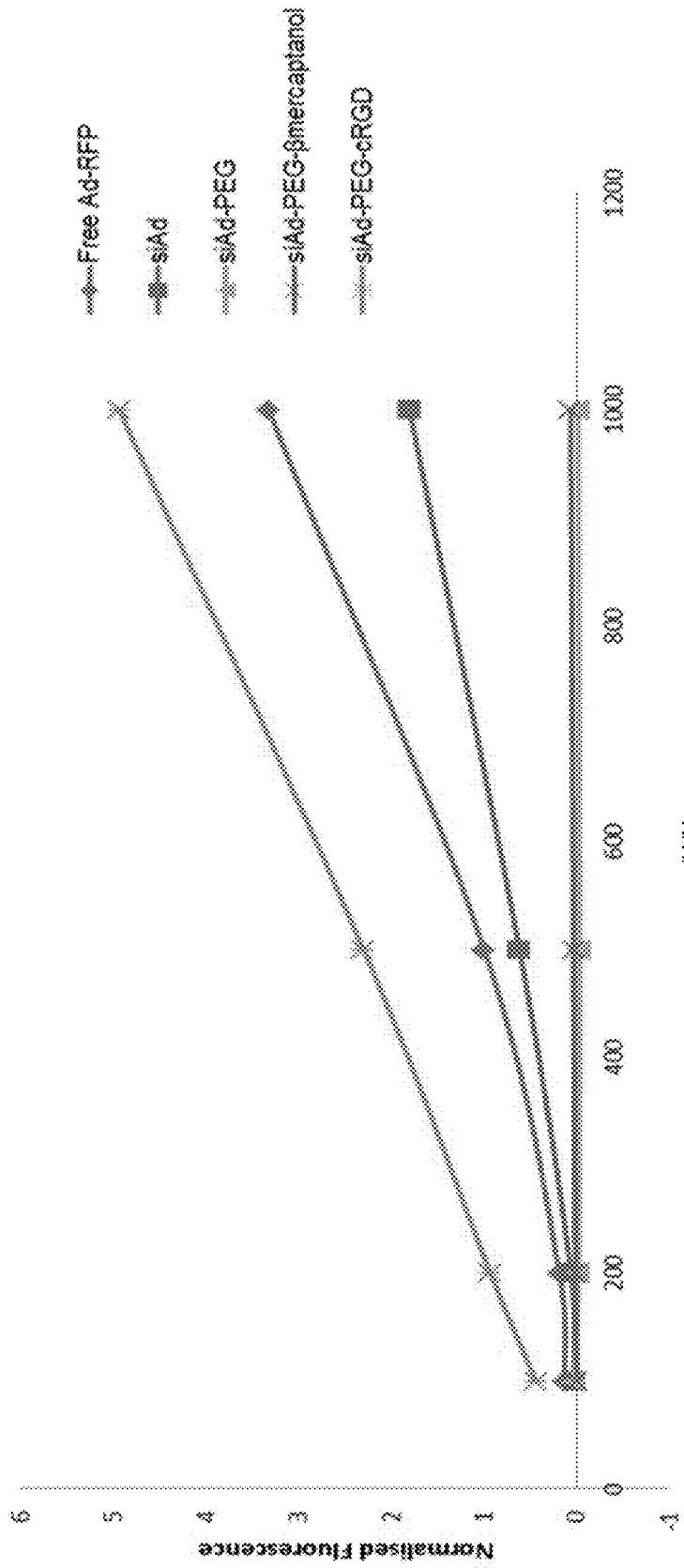
FIG. 5 shows a data plot of exemplary implementations for retargeting of the exemplary silica-coated biological entity.

FIG. 2A shows a data plot depicting the transduction efficiency of an exemplary Adenovirus-RFP bioagent payload after coating with an exemplary silica nanostructure. RFP fluorescence intensity was measured two days post transduction with setups normalized to the MOI 500 level. The exemplary silica-coated adenoviruses maintained transduction activity and were protected from proteinase K digest. An exemplary secondary coating of PEG on the silica particle was sufficient to ablate transduction.

FIG. 2B shows a data plot depicting the FACS analysis (e.g., fluorescence-activated cell sorting, using flow cytometry) of cells transduced with free adenovirus-RFP or silica-coated adenovirus-RFP. Cells were infected with Ad-RFP then harvested and analyzed on FACS two days post transduction. Both free and silica-coated Ad-RFP showed population wide dose response with increasing viral titer.

FIG. 2C shows a data image showing in vivo activity of the exemplary silica-coated adenoviruses. An exemplary C57/Bl6 nu/nu mouse bearing bilateral HT1080 tumors was given two injections of $5\times10^7$ pfu free firefly luciferase encoding adenoviruses (Ad-Luc) intratumoral (IT) to the right tumor and two doses of $5\times10^7$ pfu silica-coated Ad-Luc IT to the left tumor. Luciferase expression was analyzed after 4 days post injection by giving 50 μL 0.2 mg/mL d-luciferin IV.

The disclosed technology is also capable to co-encapsulate various moieties that confer added functionality with our viruses. For example, a perfluorocarbon nanoemulsion can be included to allow for ultrasound triggered release of the virus. In one such exemplary implementation of the method to co-encapsulate an exemplary moiety, a fluorocarbon emulsion is stabilized by a negatively charged surfactant. The emulsion is reacted with a cationic polymer, e.g., such as poly-L-lysine (PLL), followed by adsorption of negatively charged viruses. Finally, silica poly-condensation reaction is performed on the surface encapsulating emulsion together with viruses in silica.

FIG. 3 shows a process diagram of an exemplary method for co-encapsulation of one or more biological entities with targeting moieties in the nanostructure enclosure, in which the nanostructure enclosure preserves the biological activity of the encapsulated biological entities while providing a targeting release mechanism. The method includes a process to bind a surface-charged material 301 with a targeting substance or moiety 302 to form a material complex 303 presenting surface charge. For example, a negatively charged nanoemulsion (NE) can be reacted with a cationic polymer, e.g., poly-L-lysine (PLL), to form a material substance having positively charged regions on the substance containing the PLL and the NE based on the PLL. The method includes a process to form a bioentity-targeting material structure 307 by reacting the surface-charged material complex 303 with a biological entity or substance 305, e.g., which binds the biological entity or substance to the material complex 303 on the surface charge. For example, as illustrated in the diagram of FIG. 3, a negatively charged virus (e.g., adenovirus) can be reacted with the cationic polymer, PLL, regions of the structure 307, e.g., in which the adenovirus is bound to the surface of the PLL-NE structure by an electrostatic force. The positively charged PLL-NE attracts negatively charged adenoviruses to its surface. Silica poly-condensation reaction is performed on the surface encapsulating emulsion together with viruses in silica. The method includes a process to produce a biological entity/targeting substance co-encapsulated nanostructure 310 by forming a nanostructure coating 309 to enclose the structure 307. For example, the exemplary positively charged virus/PLL-NE structure attracts negatively charged silica precursor and hydroxyl ions creating a basic environment suitable for the silica polycondensation reaction to form a silica nanocoating that encapsulates the viral payload with the targeting substance, e.g., the nanoemulsion.

In some exemplary implementations of the disclosed technology, viruses and targeting moieties were encapsulated in silica nanocoating structures.

All adenoviruses used in the exemplary implementations described below were non-replicative with deletions in the E1/E3 regions. To determine if the exemplary silica nanocoating had an adverse effect on the transduction efficacy of adenoviruses, free- versus silica-coated RFP-encoding adenovirus (Ad-RFP) were compared in cell culture. The exemplary results showed that silica-coated adenoviruses not only maintained activity post coating but also showed a 3-fold increase in transduction efficacy over free adenoviruses, e.g., which could be an early indication of a retargeting mechanism. Subsequent implementations using FACS analysis, for example, indicated this was a population wide phenomena and not the result of a small secondary population of super-infected cells. Furthermore, the exemplary implementations included the addition of PEG to the silica layer, which was shown to ablate transduction by the silica-coated adenoviruses. The exemplary adenoviruses encapsulated in the exemplary silica nanocoatings can also be stored at −80° C. without any lost in bioactivity. Exemplary in vivo implementations in mice showed the 3-fold higher activity from coated viruses carried over also applied in vivo.

Exemplary implementations were performed to demonstrate the protection of the silica-coated adenoviruses from neutralizing antibodies. The transduction efficacy of free and coated adenoviruses were compared post exposure to goat Ad5-anti-hexon polyclonal (e.g., obtained from Thermo Scientific PA128357) for 1 hour at 37° C. Free adenovirus showed a sharp neutralization with a inhibitory concentration 50% (IC50) of $5\times10^{-3}$ antibody dilution. The exemplary silica-coated adenovirus showed no loss of activity at the same antibody concentration.

FIG. 4 shows data plots depicting exemplary results of neutralization assays, in the presence of antibodies, to characterize the bioactivity preservation of the exemplary bioentity-encapsulated nanostructures. For example, free- and silica-coated Ad-RFP were incubated with varying dilutions of neutralizing antibodies. RFP fluorescence intensity was measured two days post transduction with setups normalized to the MOI 500 level. Transduction with free adenoviruses was significantly suppressed in the presence of neutralizing antibodies at the two exemplary antibody titers tested. The exemplary silica-nanocoated adenoviruses showed little differential impact from incubation with neutralizing antibodies, with only a modest suppression at the higher antibody titer.

Exemplary implementations were performed to demonstrate the ability to retarget adenoviruses using targeting ligands conjugated to the surface of the exemplary silica nanostructured coating. For example, exemplary silica-nanocoated Ad-RFP was used and given a secondary coating of PEG to ablate transduction. For example, Ad-RFP was coated with silica and PEG, and alternatively functionalized with cRGD or β-mercaptanol. RFP fluorescence intensity was measured 2 days post transduction with setups normalized to the MOI 500 level. FIG. 5 shows a data plot showing cRGD retargeting of silica-nanocoated Ad-RFP. The exemplary results of the implementations showed that functionalization with cRGD was sufficient to rescue PEG/silica-coated Ad-RFP from PEG ablation. β-mercaptanol functionalized PEG/silica Ad-RFP showed no recovery in transduction efficiency.

Figure 6:
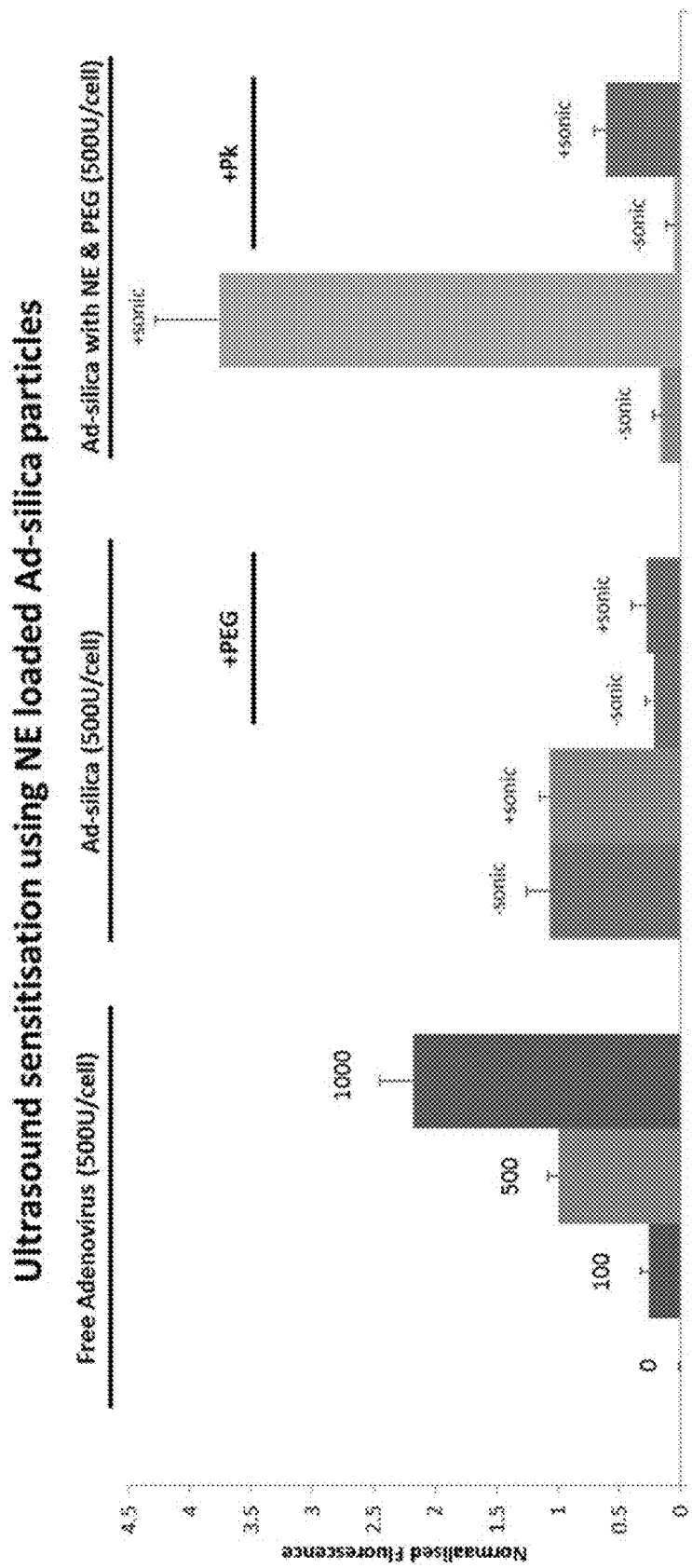
FIG. 6 shows data plots depicting ultrasound triggered release of adenoviruses from the exemplary nanostructured coatings.

Exemplary implementations were performed to demonstrate the ability to trigger viral release using ultrasound exposure. For example, silica nanocoating structures that encapsulated adenovirus (siAd-RFP) were compared to silica nanocoating structures that co-encapsulated adenovirus with a nanoemulsion (siAd-RFP-NE). FIG. 6 shows data plots depicting ultrasound triggered release of adenoviruses. The exemplary siAd-RFP and siAd-RFP-NE were alternatively exposed to ultrasound or left as-is. The exemplary siAd-RFP-NE showed a 20 fold increase in RFP transduction post exposure to ultrasound. The exemplary siAd-RFP showed no significant difference in RFP transduction post ultrasound exposure.

EXAMPLES

Some exemplary embodiments of the methods and devices of the present technology are described below.

In one example, a method to produce a bioactive payload delivery device includes forming an intermediate structure by binding a polymer material with a biological substance based on an electrostatic force, in which the formed intermediate structure includes a plurality of regions presenting a net surface charge; and forming a coating structure of a biocompatible material directly on the formed intermediate structure to enclose the biological substance, in which the coating structure preserves biological activity of the biological substance enclosed therein, thereby producing a bioactive payload delivery device.

Implementations of the exemplary method can include one or more of the following exemplary features. For example, in some implementations of the method, the coating structure can include a nanoparticle having a size in the nanometer regime, e.g., such as 1 nm to 999 nm. For example, the biological substance can include a virus, bacteria, protein, enzyme, prodrug (e.g., a drug precursor molecule that can be converted into a more reactive form by some physical or chemical means), and/or nucleic acid vector, e.g., such as a DNA vector or an RNA vector. For example, the biocompatible material used to form the coating structure can include silica. In some implementations of the method, for example, the forming the intermediate structure can include cross-reacting the biological substance with a poly-cationic polymer material to form a positively-charged surface in the plurality of regions of the intermediate structure. For example, the poly-cationic polymer material can include poly-l-lysine. In some implementations of the method, for example, the forming the coating structure can include a charge-mediated silica sol-gel condensation reaction directly onto the surface of the intermediate structure, in which the formed coating structure includes an enveloping silica matrix encapsulating the biological substance. In some implementations, for example, the method can further include, prior to the forming the coating structure, binding a targeting moiety to the intermediate structure to enable controlled release of the biological substance from the coating structure. For example, in some implementations, the method can further include deploying the produced bioactive payload delivery device in a fluidic media to a target substance; and applying an external triggering signal to an area including or proximate to the target substance to cause the targeting moiety to release the biological substance from the coating structure to the target substance.

Implementations of the exemplary method can include one or more of the following exemplary features. In some implementations, for example, the method can include adding a sensitizing agent to produce ultrasound triggered cavitation centers inside the coating structure, in which the adding the sensitizing agent is implemented prior to the forming the coating structure. For example, the sensitizing agent can include a fluorocarbon nanoemulsion. For example, the method can further include delivering the biological substance to a target cell or tissue in a living organism, in which the delivering can include injecting the produced bioactive payload delivery device through vasculature of the body, e.g., in which the bioactive payload delivery device extravasates from the vasculature to the target cell or tissue; and applying acoustic energy (e.g., an ultrasound pulse(s)) to an area of the living organism including or proximate to the target cell or tissue to cause the sensitizing agent to rupture the coating structure and release the biological substance to the target cell or tissue.

Implementations of the exemplary method can include one or more of the following exemplary features. In some implementations, for example, the method can include adding a pharmaceutical drug or a therapeutic agent with the intermediate structure to be enclosed in the coating structure, in which the adding the pharmaceutical drug or the therapeutic agent is implemented prior to the forming the coating structure. In some implementations, for example, the method can include adding an iron oxide constituent or other nanoscale material with the biocompatible material to form the coating structure, in which the added iron oxide constituent or the other nanoscale material provides an agent to enhance imaging of the coating structure. For example, the coating structure can stabilize the biological substance enclosed therein, thereby allowing thermal stability at temperatures including 80° C. to −37° C. In some implementations, for example, the method can include lyophilizing or critical point drying the produced bioactive payload delivery device, in which the coating structure preserves biological activity of the biological substance enclosed within the lyophilized or critical point dried bioactive payload delivery device.

Implementations of the exemplary method can include one or more of the following exemplary features. In some implementations, for example, the method can include functionalizing an exterior surface of the coating structure. For example, in some implementations, the functionalizing can include adding polyethylene glycol (PEG) to provide a secondary coating capable of preventing an immune system response within a living organism in which the bioactive payload delivery device is deployed. For example, in some implementations, the functionalizing can include attaching a targeting ligand capable of selectively binding to a particular region of a cell or tissue of a living organism in which the bioactive payload delivery device is deployed. For example, in some implementations, the functionalizing can include attaching an environmental sensing moiety to the external surface, the environmental sensing moiety capable of chemically changing form based on at least one of a redox reaction, hypoxic reaction, or acidic pH in a local environment to which the bioactive payload delivery device is deployed.

In one example, a bioactive payload delivery device includes an interior material structure including a polymer material and a biological substance that are bound to each other via an electrostatic interaction, in which the interior material structure includes a plurality of regions presenting a net surface charge, and an exterior nanostructure formed of a biocompatible material to encapsulate the interior structured material, thus preserving biological activity of the encapsulated biological substance.

Implementations of the exemplary device can include one or more of the following exemplary features. For example, the exterior nanostructure of the device can protect the biological substance from degradation from external environmental factors, e.g., including pH, temperature, pressure, and chemical substances, in an environment where the bioactive payload delivery device may be deployed. For example, the outer surface of the exterior nanostructure of the device can be functionalized with a tumor targeting ligand to cause the bioactive payload delivery device to selectively accumulate in a particular tumor region over other tissues. For example, the outer surface of the exterior nanostructure of the device can be functionalized with an agent to increase circulation time by reducing uptake from undesired body tissues, organs, and systems, e.g., in which the agent includes polyethylene glycol, a zwitterionic compound, and/or a patient-specific coating such as cell membranes. For example, the biological substance can include a virus, bacteria, protein, enzyme, prodrug, or nucleic acid vector (e.g., such as a DNA vector or an RNA vector). For example, the biocompatible material can include silica.

Implementations of the exemplary device can include one or more of the following exemplary features. In some implementations, for example, the device further can include an acoustic sensitizing agent coupled to the interior material structure to produce ultrasound triggered cavitation centers inside the exterior nanostructure. For example, the acoustic sensitizing agent can include a fluorocarbon nanoemulsion. For example, when the device is deployed in a living organism, the exterior nanostructure of the device can be caused to rupture based on an applied acoustic pulse (e.g., ultrasound pulse) to release the biological substance within the living organism.

Implementations of the exemplary device can include one or more of the following exemplary features. In some implementations, for example, the device further can include an external coating formed of polyethylene glycol (PEG) on the outer surface of the exterior nanostructure, in which the external coating is capable of preventing an immune system response within a living organism when the device is deployed. In some implementations, for example, the device further can include a targeting ligand formed on the outer surface of the exterior nanostructure, in which the targeting ligand is capable of selectively binding to a particular region of a cell or tissue of a living organism when the device is deployed. In some implementations, for example, the device further can include an environmental sensing moiety formed on the outer surface of the exterior nanostructure, in which the environmental sensing moiety is capable of chemically changing form to release the biological substance based on at least one of a redox reaction, hypoxic reaction, or acidic pH in a local environment to which the device is deployed.

In one example, a method for encapsulating a biological substance includes forming a biocompatible material onto a biological structure to form a coating structure enclosing the biological structure, the coating structure having a size in the nanometer range, in which the biological structure preserves biological activity within the coating structure.

Implementations of the exemplary method can include one or more of the following exemplary features. In some implementations, for example, the method can further include forming the biological structure comprising by cross-reacting a biological substance with a poly-cationic polymer material to form a positively-charged surface in the plurality of regions of the biological structure. For example, the biological substance can include a virus, bacteria, protein, enzyme, prodrug, and/or nucleic acid vector including a DNA or an RNA. For example, the biocompatible material can include silica. For example, the poly-cationic polymer material can include poly-l-lysine. In some implementations, for example, the forming the coating structure can include a charge-mediated silica sol-gel condensation reaction directly onto the surface of the biological structure, in which the formed coating structure includes an enveloping silica matrix encapsulating the biological structure. In some implementations, for example, the method can further include attaching a sensitizing agent to the biological structure, prior to the forming the biological material onto the biological structure, to produce ultrasound triggered cavitation centers inside the coating structure. For example, the sensitizing agent can include a fluorocarbon nanoemulsion.

Further Examples

The following examples are illustrative of several embodiments of the present technology. Other exemplary embodiments of the present technology may be presented prior to the following listed examples, or after the following listed examples.

In one example of the present technology (example 1), a method of encapsulating a biological entity includes templating a biocompatible material onto a biological structure to form a coating structure enclosing the biological structure, the coating structure having a size in the nanometer range, in which the coated biological structure preserves its biological activity within the coating structure.

In another example of the present technology (example 2), a method of encapsulating a biological entity includes using a biocompatible material to form outside a biological structure of a dimension in a nanometer range as a coating structure to enclose the biological structure and to preserve biological activity of the biological structure.

Example 3 includes the method of example 1 or 2, in which the biological structure includes a virus.

Example 4 includes the method of example 1 or 2, in which the biocompatible material includes silica.

Example 5 includes the method of example 1 or 2, which further includes using an external triggering mechanism to release the biological structure from the coating structure.

Example 6 includes the method of example 1 or 2, which further includes using a targeting moiety incorporated in the coating structure to release the biological structure from the coating structure.

Example 7 includes the method of example 1 or 2, which further includes altering the surface charge on the biological structure, the altering including cross-reacting the biological structure with a poly-cationic substrate to form a positively charged surface compatible with the templating process.

Example 8 includes the method of example 7, in which the poly-cationic substrate includes poly-l-lysine.

Example 9 includes the method of example 1 or 2, which further includes implementing a charge-mediated silica sol-gel condensation reaction directly onto the surface of the biological structure to form an enveloping silica matrix forming the coating structure around the biological structure.

Example 10 includes the method of example 1 or 2, which further includes adding a sensitizing agent comprising a nanoemulsion to form ultrasound triggered cavitation centers in the coating structure, in which the adding the sensitizing agent is implemented prior to the templating.

Example 11 includes the method of example 10, in which the sensitizing agent includes fluorocarbon emulsions.

Example 12 includes the method of example 1 or 2, in which the templating includes including one or more of a drug or a therapeutic agent with the biological structure to be enclosed in the coating structure.

Example 13 includes the method of example 1 or 2, in which the templating includes adding an iron oxide constituent or other nanoscale material with the biocompatible material to form the coating structure, the iron oxide constituent or the other nanoscale material providing an agent to enhance imaging of the coating structure.

Example 14 includes the method of example 1 or 2, which further includes functionalizing the surface of the coating structure.

Example 15 includes the method of example 14, in which the functionalizing includes adding polyethylene glycol (PEG) using silane chemistry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of making a bioactive virus delivery device, the method comprising:
   binding an interior polymer material to a virus, wherein the polymer material is bound to the surface of the virus via an electrostatic interaction; and
   forming an exterior silica gel matrix directly on the surface of the interior polymer material and virus to envelope, encapsulate, and preserve biological activity of the virus, wherein an outer surface of the silica gel matrix comprises a secondary functionalization, wherein the exterior silica gel matrix does not include the interior polymer material, and wherein encapsulation of the virus by the silica gel matrix protects the virus from immune recognition and neutralization during a viral therapy.

2. The method of claim 1, wherein the exterior silica gel matrix protects the virus from degradation from external environmental factors including pH, temperature, pressure, and chemical substances in an environment where the bioactive virus delivery device is deployed.

3. The method of claim 1, wherein the secondary functionalization is a tumor targeting ligand to cause the bioactive virus delivery device to selectively accumulate in a tumor region over other tissues.

4. The method of claim 1, wherein the secondary functionalization is an agent to increase circulation time by reducing uptake from undesired body tissues, organs, and systems, the agent including at least one of polyethylene glycol, a zwitterionic compound, or a patient-specific coating such as cell membranes.

5. The method of claim 1, wherein the secondary functionalization includes an external coating formed of polyethylene glycol (PEG) on the outer surface of the exterior silica gel matrix, the external coating capable of preventing an immune system response within a living organism when the device is deployed.

6. The method of claim 1, wherein the secondary functionalization includes a targeting ligand formed on the outer surface of the exterior silica gel matrix, the targeting ligand capable of selectively binding to a particular region of a cell or tissue of a living organism when the device is deployed.

7. The method of claim 1, wherein the secondary functionalization is selected from the group consisting of: PEG, folate, pH sensitive PEG, affibodies, antibodies, IgG, IgM, VEGF-C, cRGD, DNA, aptamers, proteins, lipoproteins, apolipoproteins, glycoproteins, glycans, carbohydrates, saccharides, oligosaccharides, polymers, oligomers, and lipids.

8. The method of claim 1, wherein the secondary functionalization is PEG.

9. The method of claim 1, wherein the secondary functionalization is folate.

10. The method of claim 1, wherein the secondary functionalization is PEG and folate.

11. The method of claim 1, wherein the binding an interior polymer material to a virus includes cross-reacting the virus with a poly-cationic polymer material to form a positively-charged surface in a plurality of regions.

12. The method of claim 11, wherein the poly-cationic polymer material includes poly-l-lysine.

13. The method of claim 1, wherein the forming an exterior silica gel matrix includes a charge-mediated silica sol-gel condensation reaction directly onto the surface of the interior polymer material and virus.

14. The method of claim 1, wherein the exterior silica gel matrix includes a nanoparticle sized in a nanometer regime.

15. The method of claim 14, wherein the exterior silica gel matrix includes a nanoparticle sized from 1 nm to 999 nm.

* * * * *